(12) United States Patent
Hua et al.

(10) Patent No.: US 11,814,339 B2
(45) Date of Patent: Nov. 14, 2023

(54) METHOD FOR PREPARING ISOCYANATE IN GASEOUS PHASE

(71) Applicants: WANHUA CHEMICAL GROUP CO., LTD., Shandong (CN); WANHUA CHEMICAL (NINGBO) CO., LTD., Ningbo (CN)

(72) Inventors: Weiqi Hua, Shandong (CN); Tonghe Li, Shandong (CN); Yonghua Shang, Shandong (CN); Shuchang Sun, Shandong (CN); Jingxu Wang, Shandong (CN); Jinping Han, Shandong (CN); Qiang Li, Shandong (CN); Wenbin Li, Shandong (CN); Jing Li, Shandong (CN); Pengfei Wang, Shandong (CN); Yuan Li, Shandong (CN)

(73) Assignees: WANHUA CHEMICAL GROUP CO., LTD., Shandong (CN); WANHUA CHEMICAL (NINGBO) CO., LTD., Ningbo (CN)

( * ) Notice: Subject to any disclaimer, the term of this patent is extended or adjusted under 35 U.S.C. 154(b) by 0 days.

(21) Appl. No.: 17/295,806

(22) PCT Filed: Dec. 26, 2018

(86) PCT No.: PCT/CN2018/123876
§ 371 (c)(1),
(2) Date: May 20, 2021

(87) PCT Pub. No.: WO2020/132936
PCT Pub. Date: Jul. 2, 2020

(65) Prior Publication Data
US 2022/0024863 A1   Jan. 27, 2022

(51) Int. Cl.
*C07C 263/10* (2006.01)
*C07C 265/06* (2006.01)

(52) U.S. Cl.
CPC .......... *C07C 263/10* (2013.01); *C07C 265/06* (2013.01)

(58) Field of Classification Search
CPC ........ A61K 2800/75; A61K 8/60; A61K 8/73; A61K 8/99; A61K 8/361; A61K 8/9789; A61Q 19/00; A61Q 19/005; A61Q 19/007; C07C 263/10; C07C 265/06; C07C 265/14; Y02E 60/10; B29C 45/0001; B29C 45/14639; B29C 45/1866; B29C 45/46; B29C 45/7646; B29C 45/78; B29K 2105/16; C08G 18/42; C08K 3/013; H01M 10/653; H01M 50/20; H01M 50/24; H01M 50/204; H01M 50/227; C08L 101/00
See application file for complete search history.

(56) References Cited

U.S. PATENT DOCUMENTS

| | | | | |
|---|---|---|---|---|
| 2007/0232827 | A1* | 10/2007 | Wolfert | C07C 263/10 560/347 |
| 2012/0123152 | A1* | 5/2012 | Bruns | C01B 32/80 560/347 |

FOREIGN PATENT DOCUMENTS

| | | |
|---|---|---|
| CN | 101200437 A | 6/2008 |
| CN | 101583594 A | 11/2009 |
| CN | 101698652 A | 4/2010 |
| CN | 101747232 A | 6/2010 |
| CN | 101774948 A | 7/2010 |
| CN | 102060295 A | 5/2011 |
| DE | 102005037328 A1 | 2/2007 |
| DE | 102009032413 A1 | 1/2011 |
| EP | 0593334 A1 | 4/1994 |
| EP | 0699657 B1 | 3/2002 |
| EP | 2111392 B1 | 8/2012 |
| GB | 737442 A | 9/1955 |
| JP | 2008500296 A | 1/2008 |
| WO | 2010016540 A1 | 2/2010 |
| WO | 2012130788 A1 | 10/2012 |

OTHER PUBLICATIONS

Ma, et al.: "Production and Technology Progress of Aliphatic Diisocyanates", Paint& Coating Ind., 35(12), (2005), pp. 35-40, with English abstract.
International Search Report issued in PCT/CN2018/123876 dated Sep. 26, 2019.

(Continued)

*Primary Examiner* — Jafar F Parsa
*Assistant Examiner* — Blaine G Doletski
(74) *Attorney, Agent, or Firm* — Norton Rose Fulbright US LLP; James R. Crawford

(57) ABSTRACT

A method for preparing an isocyanate in a gaseous phase by feeding, in the presence or absence of an inert gas, an amine-containing gas stream and a phosgene-containing gas stream into a reaction region, allowing the amine and the phosgene to contact in gaseous forms and undergo a phosgenation reaction in the reaction region, thus preparing the target isocyanate in a gaseous form in the reaction region. The phosgene-containing stream is subjected to preheating and warming before being fed into the reaction region, and the phosgene-containing stream comprises a substance A at a mass fraction of <1% before being subjected to the preheating and warming up. Substance A is a NCO group-containing substance and/or an olefinic double bond-containing substance. The method reduces the formation of clogging matter in a heat exchanger and a vessel during the preheating and warming of the phosgene and during the reaction process.

18 Claims, No Drawings

(56) References Cited

OTHER PUBLICATIONS

Office Action dated Dec. 24, 2020 by the CIPO in the corresponding Patent Application No. 201811602983.0, with English translation.
Office Action dated Apr. 27, 2022 by the JPO in the corresponding Patent Application No. 2021-520423, with English translation.

* cited by examiner

METHOD FOR PREPARING ISOCYANATE IN GASEOUS PHASE

CROSS REFERENCE TO RELATED APPLICATIONS

This application is a national phase under 35 U.S.C. § 371 of International Application No. PCT/CN2018/123876 filed on Dec. 26, 2018, which is hereby incorporated by reference in its entirety.

TECHNICAL FIELD

The present disclosure relates to a method for preparing an isocyanate in a gas phase and, in particular, to a method for preparing an isocyanate which can effectively reduce the coking of a heating system and a reaction system of phosgene.

BACKGROUND

Corresponding isocyanates can be prepared by the phosgenation reaction of aliphatic or alicyclic or aromatic amines in a gas phase. Phosgenation in a gas phase is generally carried out at 200-600° C. Due to high temperatures, the design of a method must meet special requirements, so as to implement the method stably for a long term without increasing the risk of phosgene leakage due to frequent maintenance.

Early patent applications such as EP593334B1 and EP699657B1 have disclosed the possibility of utilizing or destroying phosgene or hydrogen chloride gas without a study on specific problems related to the recycle of phosgene. In processes of modern industrial production, considering safety, environmental protection, and economy, phosgene is recycled and reused in phosgenation processes.

Patent Nos. DE102009032413.5 and GB737442 both describe a method for phosgene recycle and circulation in a process of synthesizing an isocyanate through phosgenation. GB737442 describes an index that the content of HCl in the recycled phosgene is 0.5-0.7%.

Patent No. CN103796991A limits the content of CO in phosgene in a phosgenation process in a gas phase. A first stream with a low content of CO (<1%) is used as a reaction stream during the phosgenation of an amine in a gas phase to produce an isocyanate, solving the problem of the decomposition of phosgene into carbon monoxide and chlorine at a high temperature.

Patent No. EP2111392 discloses the mass fraction of chlorine in the phosgene-containing stream before mixing with the amine-containing stream being less than 1000 ppm by weight and/or the mass fraction of bromine in the phosgene-containing stream being less than 50 ppm by weight. Accordingly, the problem of chlorine corrosion at high temperatures in a phosgenation method in a gas phase is solved, and the content of bromine in phosgene is controlled so that the problem of an undesired increase in chromaticity caused by a downstream isocyanate is solved.

Patent No. DE102005037328.3 requires the separation of hydrogen chloride from a recycled phosgene stream during a phosgenation reaction in a gas phase so that the mass fraction of hydrogen chloride in a phosgene-containing stream is smaller than 15 wt % before the phosgene-containing stream is mixed with a diamine-containing stream.

SUMMARY

The present disclosure provides a method for preparing an isocyanate in a gas phase. The method can effectively avoid blockages in heat exchangers and equipments in a heating and reaction process of phosgene and reduce the generation of blockages, thereby obtaining a longer operation period, reducing the frequency of maintenance of a phosgene-containing system, and improving the operation safety of a device.

To achieve the preceding object, the present disclosure provides technical solutions described below.

A method for preparing an isocyanate in a gas phase includes: feeding an amine-containing gas stream and a phosgene-containing stream into a reaction zone in the presence or absence of an inert gas, allowing the amine and the phosgene to contact in gaseous forms and undergo a phosgenation reaction in the reaction zone, thus preparing a gaseous target isocyanate in the reaction zone; where the phosgene-containing stream is preheated before entering the reaction zone and the phosgene-containing stream comprises a substance A with a mass fraction smaller than 1% before being preheated, where the substance A is a substance containing NCO groups and/or olefinic double bonds.

In some preferred embodiments, the mass fraction of the substance A contained in the phosgene-containing stream before the phosgene-containing stream is preheated is preferably controlled to be smaller than 0.5%, more preferably smaller than 0.1%. Of course, the mass fraction of the substance A may be controlled at a lower level.

In the phosgenation process in a gas phase, both the amine and the phosgene need to stay in a gaseous state. Before the reaction, both the amine-containing stream and the phosgene-containing stream are preheated to a temperature higher than 200° C., for example, 200-600° C., preferably 200-450° C. After the amine-containing stream and the phosgene-containing stream enter the reaction zone, the temperature of the reaction zone is controlled at 200-600° C., preferably 200-450° C. The stability of reaction materials and reaction products at high temperatures is an important factor for the phosgenation reaction in a gas phase. To shorten the residence time of the amine and the isocyanate at high temperatures, in the methods in the existing art, for example, the residence time of the amine at high temperatures needs to be shortened as much as possible in a heating and gasification process. At the same time, since the isocyanate produced in the reaction is unstable at high temperatures, isocyanate gas produced in the reaction needs to be quickly cooled to a stable state at low temperatures. Although the residence time of the amine and the isocyanate at high temperatures is shortened by different methods as much as possible in the existing art, it is still difficult to prevent the problems such as chain breakage, decomposition, and polymerization of the amine and the isocyanate at high temperatures.

An organic amine (simply referred to as amine) used for preparing the isocyanate will break or decompose at high temperatures into small molecular amines or components containing olefinic double bonds. These components resulting from the decomposition enter a photochemical reactor along with the amine-containing stream so that the corresponding small molecular isocyanates or components containing olefin double bonds are produced. The target isocyanate produced in the phosgenation reaction in a gas phase (that is, the isocyanate expected to be produced in the production process) will also break and decompose at high temperatures into small molecular isocyanates or components containing olefinic double bonds. The substance containing NCO groups and/or the substance containing olefinic double bonds involved in the substance A in the present disclosure refer to these above undesired substances containing NCO groups (non-target isocyanate) and/or components containing olefinic double bonds.

Both the amine and the isocyanate will decompose and react at high temperatures to produce small molecular isocyanates or substances containing olefinic double bonds. These small molecular isocyanates or substances containing olefinic double bonds not only have low boiling points but also are easy to distribute in a circulating phosgene stream in the process of recycling and reusing phosgene. Moreover, since these small molecular isocyanates have very high reaction activity and double bonds in the substances containing olefinic double bonds are easy to polymerize, it is easier to produce polymers when they are heated so that tar and blockages are formed. In the phosgenation reaction in a gas phase, the phosgene stream needs to be heated to 200-600° C. and the temperature of the phosgenation reaction is also in the range of 200-600° C. Therefore, in the heating and reaction process of the phosgene, NCO-based substances and/or olefin-based substances contained in the phosgene are prone to polymerization, resulting in the coking of heat exchangers and reaction equipments and problems such as decreased heat exchange capability, the blockage of heat exchangers, the blockage of the reaction system, and increased side reactions, and affecting the operation period of the device. The inventors of the present application have found that before the phosgene-containing stream is preheated, the mass fraction of the substance A (the substance containing NCO groups and/or the substance containing olefinic double bonds) contained in the phosgene-containing stream is controlled to be smaller than 1%, preferably 0.5%, more preferably 0.1% so that these problems can be effectively solved, the blockage of heat exchangers and the blockage of the reaction system can be effectively avoided, and the operation period of the device can be prolonged.

In the art, in the process of preparing the isocyanate, excessive unreacted phosgene and hydrogen chloride gas are separated from a substantially gaseous reaction mixture obtained in the reaction zone, and at least part of the excessive phosgene that has been separated is recycled to the reaction zone. This type of phosgene is referred to as circulating phosgene. The phosgene in the phosgene-containing stream of the present disclosure includes fresh phosgene and/or circulating phosgene. The phosgene-containing stream may be introduced into the reaction zone (reaction space) through a single phosgene-containing stream or by feeding multiple phosgene-containing substreams. In the case where the phosgene-containing stream is introduced into the reaction zone through more than two phosgene-containing substreams, the phosgene-containing substreams are added together to the reaction zone to form the total phosgene-containing stream (or referred to as the phosgene stream). The mass fraction of the substance A (that is, the substance containing NCO groups and/or the substance containing olefinic double bonds) in the phosgene stream depends on the mass fractions of the substance A in each phosgene-containing substream. In this case, the mass fraction of the substance A in the total phosgene-containing stream is calculated in this manner. In the substance A, for the substance containing NCO groups, the calculation of the content does not include the target isocyanate that is to be prepared in the reaction and may be contained in the phosgene-containing stream.

Various phosgene-containing substreams (for example, the circulating phosgene and the fresh phosgene) may be combined into the total phosgene-containing stream before introduced into the reaction zone and then fed into the reaction space. Multiple substreams (which may be the circulating phosgene, the fresh phosgene, or a mixture thereof in various cases) may be introduced into the reaction space at the same position or different positions, thereby introducing the phosgene-containing stream during the reaction.

In the present disclosure, the term "fresh phosgene" refers to a phosgene-containing stream that is not recycled from the phosgenation reaction and has not undergone any reaction stage involved in the phosgenation reaction after phosgene therein is generally synthesized from chlorine and carbon monoxide.

At the initial stage of start-up of the reaction device for preparing the isocyanate, the phosgene used for the reaction mainly comes from fresh phosgene. After the device operates stably, the mass fraction of NCO-based substances (that is, substances containing NCO groups) and/or substances containing olefinic double bonds in the circulating phosgene will gradually increase under the effect of the decomposition of the amine and the isocyanate in the phosgenation reaction at high temperatures, so that a series of undesired blockages are produced in the heating and reaction process of the phosgene stream and cause an irreversible effect on the reaction. Therefore, after the start-up of the reaction, it is necessary to control the average mass fraction of the substance A (NCO-containing substances and/or substances containing olefinic double bonds) in the phosgene-containing stream before it is preheated to be smaller than 1%.

In the present disclosure, the circulating phosgene is obtained from the reaction mixture by well-known methods in the art (for example, the corresponding contents have been disclosed in patent document GB737442A), which is not the focus of the present disclosure and not repeated here one by one.

The mass fraction of the substance A (NCO-containing substances and/or substances containing olefinic double bonds) in the phosgene-containing stream may be controlled to be smaller than 1% in a manner that the NCO-containing substances and/or the substances containing olefinic double bonds in the stream are removed. The mass fraction may be controlled by a conventional separation method known in the art. In the present disclosure, the substance A (NCO-containing substances and/or substances containing olefinic double bonds) in the phosgene-containing stream before it is preheated may be directly removed by an existing separation method, which is not particularly limited as long as the mass fraction of the substance A (NCO-containing substances and/or substances containing olefinic double bonds) can be controlled within the required range, for example, one or a combination of several of rectification, adsorption, scrubbing, or other similar methods. In some embodiments, the mass fraction of the substance A contained in the phosgene-containing stream before the phosgene-containing stream is preheated is controlled through one or a combination of at least two of rectification, adsorption, or scrubbing.

The NCO-containing substances and/or the substances containing olefinic double bonds in the phosgene stream are preferably controlled through rectification and/or scrubbing or through a combination of rectification and scrubbing. A preferred scrubbing medium preferably adopts the same solvent as the reaction, where the solvent is preferably one or a combination of at least two of toluene, xylene, chlorobenzene, dichlorobenzene, or the like. In the combination of rectification and scrubbing, the scrubbing medium is used for washing the NCO-containing substances and/or the substances containing olefinic double bonds out of the phosgene stream that contains the NCO-containing substances and/or the substances containing olefinic double bonds, so as to obtain a phosgene stream containing a certain content of the NCO-containing substances and/or the substances containing olefinic double bonds and obtain a scrubbing stream containing phosgene, NCO-containing substances and/or substances containing olefinic double bonds. Preferably, the scrubbing stream containing phosgene is returned to a phosgene refining system. After reaching a certain content, the NCO-containing substances and/or the substances containing olefinic double bonds in the scrubbing stream may be separated from the scrubbing stream through rectification, so as to obtain substances containing NCO and/or olefinic double bonds. Scrubbing and rectification may be carried out at 1 to 10 bar (absolute pressure), preferably 1 to 5 bar (absolute pressure).

In some embodiments, substances containing NCO and/or olefinic double bonds in the phosgene stream are separated through adsorption. For example, the circulating phosgene stream obtained from a phosgene circulation system may be adsorbed by an adsorption unit, preferably activated carbon, so as to control the content of NCO-containing substances and/or substances containing olefin olefin double bonds in circulating phosgene within a certain range.

In some embodiments, the circulating phosgene subjected to separation is mixed with fresh phosgene to obtain a phosgene stream in which the content of the substance A (NCO-containing substances and/or substances containing olefinic double bonds) is smaller than 1%.

In the present disclosure, the phosgene-containing stream may contain 0-10 wt % of HCl gas.

An additional inert medium (or the "inert gas" in the present disclosure) may be used in the method of the present disclosure. The inert medium is a medium that is in a gaseous form at the reaction temperature and does not react with a compound present during the reaction in the reaction space. The inert medium is generally mixed with the amine and/or the phosgene before the reaction or may also be introduced separately. For example, one or a combination of several of nitrogen, rare gases such as helium or argon, or aromatic compounds such as chlorobenzene, dichlorobenzene, xylene, carbon dioxide, or carbon monoxide may be used. Preferably, nitrogen and/or chlorobenzene are used as the inert medium. The inert medium is added to the amine-containing stream or the phosgene-containing stream such that the volume ratio of the inert medium to the amine or the phosgene is 0-20:1. If one or more additional inert streams are fed into the phosgene-containing stream, these gas streams are involved in the calculation of the phosgene-containing stream as substreams of the total phosgene-containing stream in the practice of the method of the present disclosure. That is, when the mass fraction of the substance A (NCO-containing substances and/or substances containing olefinic double bonds) in the phosgene-containing stream is calculated, these gas streams are taken into consideration.

In some embodiments, the amine-containing gas stream further contains the inert gas, where the volume ratio of the inert gas to the amine is 0-20:1 and the inert gas is introduced into the reaction zone by being added to the amine-containing gas stream.

Additionally/alternatively, the phosgene-containing stream further contains the inert gas, where the volume ratio of the inert gas to the phosgene is 0-20:1 and the inert gas is introduced into the reaction zone by being added to the phosgene-containing stream.

In some embodiments, in the reaction zone, the phosgene reacts with the amine at an absolute pressure of 0.01-0.5 Mpa, preferably 0.07-0.3 MPa, more preferably 0.09-0.2 MPa. In the method of the present disclosure, based on the common pressure in the reaction zone, the temperature of the reaction zone is selected to be higher than the boiling point of the amine used. The temperature of the reaction zone is generally controlled at 200-600° C., preferably 250-450° C.

In some embodiments, the phosgene reacts with the amine in the reaction zone for an average reaction time (or referred to as an average contact time) of 0.01-15 s, preferably 0.05-10 s, more preferably 0.1-5 s. The average reaction time is a duration when the amine begins to be mixed with the phosgene to when the reaction mixture leaves the reaction space (reaction zone) and enters a post-treatment stage.

When the isocyanate is prepared in a gas phase, the phosgene is used in excess compared with the amine (i.e., stoichiometric excess). In some embodiments, the molar ratio of the phosgene to the amino groups in the amine is 2.2-20:1, for example, 2.2:1, 5:1, 10:1, 15:1, 20:1, or the like, preferably 4-10:1, more preferably 6-8:1.

In some embodiments, the amine-containing gas stream and the phosgene-containing stream enter the reaction zone at a flow rate of 5-100 m/s, preferably 10-80 m/s, respectively.

The target isocyanate has a general formula of $R(NCO)_n$ and is determined based on production requirements. For example, the target isocyanate may be one or a combination of at least two of aliphatic, alicyclic, or aromatic isocyanates, which is not particularly limited. Preferably, R is aliphatic, alicyclic, or aromatic hydrocarbyl having 4-15 carbon atoms and n is an integer from 1 to 10. Preferably, the target isocyanate is one selected from the group consisting of phenyl isocyanate, cyclohexyl isocyanate, 1,4-butane diisocyanate, 1,3-dimethyl isocyanate cyclohexane, 1,6-hexamethylene diisocyanate, 1,4-cyclohexane diisocyanate, isophorone diisocyanate, 4,4'-dicyclohexylmethane diisocyanate, p-phenylene diisocyanate, m-xylylene diisocyanate, toluene diisocyanate, 1,8-diisocyanato-4-isocyanatomethyl octane, nonane triisocyanate, and a combination of two or more selected therefrom.

In the present disclosure, the amine used may be various amines allowed to be used for preparing isocyanates in the art. A specific amine raw material is determined based on production requirements, which is not particularly limited. In some embodiments, the amine is, for example, selected from the group consisting of aniline, cyclohexylamine, 1,4-butane diamine, 1,3-cyclohexanedimethylamine, 1,6-hexanediamine, 1,4-diaminocyclohexane, 1-amino-3,3,5-trimethyl-5-aminomethylcyclohexane, 4,4'-diaminodicyclohexylmethanediamine, p-phenylenediamine, m-xylylenediamine, 2,4-toluenediamine, 2,6-toluenediamine, 1,8-diamino-4-(aminomethyl)octane, and triaminononane.

In some embodiments, the reaction is carried out continuously, that is, raw materials are input continuously and the reaction product is output continuously.

The technical solutions provided by the present disclosure have the following beneficial effects:

The method for preparing the corresponding isocyanate by reacting the amine with the phosgene in a gas phase, provided by the present disclosure, can effectively avoid the blockages in the heat exchangers and equipments in the heating and reaction process of phosgene, thereby obtaining longer operation period, reducing the frequency of maintenance of the phosgene-containing system, and improving the operation safety of the device.

DETAILED DESCRIPTION

For a better understanding of technical solutions of the present disclosure, the content of the present disclosure is further described below in conjunction with examples and is not limited to the examples set forth below.

In the following examples or comparative examples, the mass fraction of the substance A (NCO-containing substances and/or substances containing olefinic double bonds) in a phosgene stream (that is, a phosgene-containing stream) is measured through gas chromatography. The method is as follows: the mass fraction is measured with Agilent 7890A gas chromatograph, where a column model is J&W 112-2112 CAM 15 m, 0.25 mm, 0.25 μm, a detector is FID detector, the temperature at a sample inlet is 250° C., the temperature of the column is increased by the following program: being maintained at 50° C. for 2 min, increased to 100° C. at a rate of 10° C./min and maintained at 100° C. for 2 min, and increased to 250° C. at a rate of 25° C./min and maintained at 250° C. for 2 min, and the temperature of the detector is 250° C. GC/MS is used for determining the residence time of the NCO-containing substances and/or the substances containing olefinic double bonds in the phosgene stream in the gas chromatograph. A propyl isocyanate is used as an external standard, and the mass fraction of the substance A (the NCO-containing substances and/or the substances containing olefinic double bonds) in the phosgene stream is determined by an external standard method.

In the following examples, the mass fraction of the substance A (the NCO-containing substances and/or the substances containing olefinic double bonds) in the phosgene stream is controlled through rectification. The theoretical number of plates of a packed column is 25. In the rectification process of circulating phosgene, the circulating phosgene stream is purified through continuous rectification. The pressure at the top of the column is controlled at 2 bar, the temperature at the top of the column is controlled at about 10° C., the temperature at the bottom of the column is controlled at 160° C., and the mass fraction of the substance A (the NCO-containing substances and/or the substances containing olefinic double bonds) in the phosgene stream is controlled within the required range in a manner that a reflux ratio is controlled.

Example 1

After mixed with nitrogen (where the volume ratio of nitrogen to 1,6-hexanediamine was 0.5: 1), 1,6-hexanediamine continuously reacted with phosgene in a tubular reactor, where 1,6-hexanediamine and phosgene were fed at a pressure of 0.25 MPa and a temperature of 310° C. (which was reached by preheating streams), and the absolute pressure of a reaction zone was 0.09 MPa, which was slightly lower than atmospheric pressure. The molar ratio of phosgene to 1,6-hexanediamine was 6: 1, the temperature of the reaction zone was 420° C., the streams were fed into the reactor at a flow rate of 70 m/s, and the average contact time was 2 s. The mass fraction of a substance A (NCO-containing substances and substances containing olefinic double bonds) contained in a phosgene-containing stream (composed of a stream of fresh phosgene and a stream of circulating phosgene in this example) before it was preheated and entered the tubular reactor was controlled through rectification to be 0.5% in an operation process.

After leaving the reaction zone, the reaction product entered a process zone with a pressure of 0.08 MPa and sprayed and washed with chlorobenzene. The obtained solution of 1,6-hexamethylene diisocyanate was rectified and purified to give a phosgene- and HCl-free solution of 1,6-hexamethylene diisocyanate, which was separated and purified through a subsequent rectification to give the product 1,6-hexamethylene diisocyanate. After 3 months of continuous operation of the reaction device, a pressure difference between an outlet and an inlet of a phosgene heater was about 15 Kpa. The reaction device was stopped for maintenance. The phosgene heater, pipes, and the tubular reactor had trace solids, which had no effect on the continuous operation of the reaction.

Example 2

The mass fraction of a substance A (NCO-containing substances and substances containing olefinic double bonds) contained in a phosgene-containing stream before it was preheated and entered the tubular reactor was controlled through rectification to be 0.8% in an operation process. Other experimental conditions were the same as those of Example 1 so that the product 1,6-hexamethylene diisocyanate was obtained. After 2 months of continuous operation, a pressure difference between an outlet and an inlet of a phosgene heater was about 15 Kpa. The reaction device was stopped for maintenance. The phosgene heater, pipes, and the tubular reactor had trace solids, which had no effect on the continuous operation of the reaction.

Example 3

The mass fraction of a substance A (NCO-containing substances and substances containing olefinic double bonds) contained in a phosgene-containing stream before it was preheated and entered the tubular reactor was controlled through rectification to be 0.1% in an operation process. Other experimental conditions were the same as those of Example 1 so that the product 1,6-hexamethylene diisocyanate was obtained. After 3 months of continuous operation, a pressure difference between an outlet and an inlet of a phosgene heater was maintained at about 12 Kpa. The reaction device was stopped for maintenance. The phosgene heater and pipes had no solids and the tubular reactor had trace solids, which had no effect on the continuous operation of the reaction.

Example 4

After mixed with nitrogen (where the volume ratio of nitrogen to 1-amino-3,3,5-trimethyl-5-aminomethylcyclohexane was 0.6: 1), 1-amino-3,3,5-trimethyl-5-aminomethylcyclohexane continuously reacted with phosgene in a tubular reactor, where 1-amino-3,3,5-trimethyl-5-aminomethylcyclohexane and phosgene were fed at a pressure of 0.3 MPa and a temperature of 330° C. (which was reached by preheating streams), and the absolute pressure of a reaction zone was 0.12 MPa, which was slightly higher than atmospheric pressure. The molar ratio of phosgene to 1-amino-3,3,5-trimethyl-5-aminomethylcyclohexane was 5: 1, the temperature of the reaction zone was 400° C., the streams were fed into the reactor at a flow rate of 65 m/s, and the average contact time was 1.8 s. The mass fraction of a substance A (NCO-containing substances and substances containing olefinic double bonds) contained in a phosgene-containing stream (composed of a stream of fresh phosgene and a stream of circulating phosgene) before it was preheated and entered the tubular reactor was controlled through rectification to be 0.6% in an operation process.

After leaving the reaction zone, the reaction product entered a process zone with a pressure of 0.1 MPa and sprayed and washed with chlorobenzene. The obtained solution of isophorone diisocyanate was rectified and purified to give a phosgene- and HCl-free solution of isophorone diisocyanate, which was separated and purified through a subsequent rectification to give the product isophorone diisocyanate. After 2.5 months of continuous operation of the reaction device, a pressure difference between an outlet and an inlet of a phosgene heater was about 15 Kpa. The reaction device was stopped for maintenance. The phosgene heater, pipes, and the tubular reactor had trace solids, which had no effect on the continuous operation of the reaction.

Comparative Example 1

This comparative example was basically the same as Example 1 except that the mass fraction of a substance A (NCO-containing substances and substances containing olefinic double bonds) was controlled to be 2.5% so that the product 1,6-hexamethylene diisocyanate was obtained. After 1 month of continuous operation, a pressure difference between an outlet and an inlet of a phosgene heater increased to about 50 Kpa and showed a significant change. The reaction device was stopped for maintenance. The phosgene heater, pipes, and the tubular reactor had obvious solids, which affected the continuous operation of the reaction.

Comparative Example 2

This comparative example was basically the same as Example 1 except that the mass fraction of a substance A (NCO-containing substances and substances containing olefinic double bonds) was controlled to be 1.5% so that the product 1,6-hexamethylene diisocyanate was obtained. After 2 months of continuous operation, a pressure difference between an outlet and an inlet of a phosgene heater increased to about 50 Kpa and showed a significant change. The reaction device was stopped for maintenance. The phosgene heater, pipes, and the tubular reactor had obvious solids, which affected the continuous operation of the reaction.

Comparative Example 3

This comparative example was basically the same as Example 4 except that the mass fraction of a substance A (NCO-containing substances and substances containing olefinic double bonds) was controlled to be 2.0% so that the product isophorone diisocyanate was obtained. After 1.2 months of continuous operation, a pressure difference between an outlet and an inlet of a phosgene heater increased to about 45 Kpa and showed a significant change. The reaction device was stopped for maintenance. The phosgene heater, pipes, and the tubular reactor had obvious solids, which affected the continuous operation of the reaction.

Those skilled in the art will appreciate that some modifications or adaptations may be made to the present disclosure based on the teachings of the description. These modifications or adaptations should fall within the scope of the present disclosure as defined by the claims.

What is claimed is:

1. A method for preparing an isocyanate in a gas phase, comprising: feeding an amine-containing gas stream and a phosgene-containing stream into a reaction zone in the presence or absence of an inert gas, allowing the amine and the phosgene to contact in gaseous forms and undergo a phosgenation reaction in the reaction zone, thus preparing the isocyanate in the reaction zone; wherein the phosgene-containing stream is preheated before entering the reaction zone and the phosgene-containing stream comprises a substance A with a mass fraction smaller than 0.5% before being preheated, wherein the substance A is a substance containing non-target isocyanate (NCO) groups and olefinic double bonds;

where before preheated, the phosgene-containing stream is treated through one or a combination of at least two of rectification, adsorption, and scrubbing such that the mass fraction of the substance A contained in the phosgene-containing stream is controlled.

2. The method according to claim 1, wherein the mass fraction of the substance A contained in the phosgene-containing stream before the phosgene-containing stream is preheated is smaller than 0.1%.

3. The method according claim 1, wherein before entering the reaction zone, the phosgene-containing stream is preheated to a temperature higher than 200° C.

4. The method according to claim 1, wherein before entering the reaction zone, the phosgene-containing stream is preheated to a temperature of 200-600° C.

5. The method according to claim 4, wherein before entering the reaction zone, the phosgene-containing stream is preheated to a temperature of 250-450 ° C.

6. The method according to claim 1, wherein before preheating, the phosgene-containing stream is treated through rectification and/or scrubbing.

7. The method according to claim 1, wherein the inert gas is introduced into the reaction zone by being added to the amine-containing gas stream, and the volume ratio of the inert gas to the amine is 0-20: 1; and/or the inert gas is introduced into the reaction zone by being added to the phosgene-containing stream, and the volume ratio of the inert gas to the phosgene is 0-20: 1.

8. The method according to claim 1, wherein in the reaction zone, the phosgene reacts with the amine at an absolute pressure of 0.01-0.5 Mpa.

9. The method according to claim 8, wherein the phosgene reacts with the amine in the reaction zone for an average reaction time of 0.05-10 s.

10. The method according to claim 1, wherein the molar ratio of the phosgene to the amino groups in the amine is 2.2-20: 1.

11. The method according to claim 10, wherein the molar ratio of the phosgene to the amino groups in the amine is 4-10: 1.

12. The method according to claim 1, wherein the amine-containing gas stream and the phosgene-containing stream enter the reaction zone at a flow rate of 5-100 m/s.

13. The method according to claim 12, wherein the amine-containing gas stream and the phosgene-containing stream enter the reaction zone at a flow rate of 10-80 m/s, respectively.

14. The method according to claim 1, wherein the phosgene-containing stream comprises fresh phosgene and/or circulating phosgene; and/or the phosgene-containing stream contains 0-10 wt % of HCl gas.

15. The method according to claim 1, wherein the substance containing NCO groups in the substance A does not comprise the isocyanate.

16. The method according to claim 1, wherein the isocyanate has a general formula of $R(NCO)_n$, wherein R is aliphatic, alicyclic, or aromatic hydrocarbyl having 4-15 carbon atoms and n is an integer from 1 to 10; and the amine is one selected from the group consisting of aniline, cyclohexylamine, 1,4-butane diamine, 1,3-cyclohexanedimethylamine, 1,6-hexanediamine, 1,4-diaminocyclohexane, 1-amino-3,3,5-trimethyl-5-aminomethylcyclohexane, 4,4'-diaminodicyclohexylmethanediamine, p-phenylenediamine, m-xylylenediamine, 2,4-toluenediamine, 2,6-toluenediamine, 1,8-diamino-4-(aminomethyl)octane, triaminononane, and a combination of two or more selected therefrom.

17. The method according to claim 16, wherein the isocyanate is one selected from the group consisting of phenyl isocyanate, cyclohexyl isocyanate, 1,4-butane diisocyanate, 1,3-dimethyl isocyanate cyclohexane, 1,6-hexamethylene diisocyanate, 1,4-cyclohexane diisocyanate, isophorone diisocyanate, 4,4'-dicyclohexylmethane diisocyanate, p-phenylene diisocyanate, m-xylylene diisocyanate, toluene diisocyanate, 1,8-diisocyanato-4-isocyanatomethyl octane, nonane triisocyanate, and a combination of two or more selected therefrom.

18. The method according to claim 1, wherein the method for preparing an isocyanate in a gas phase is carried out continuously.

\* \* \* \* \*